United States Patent [19]

Min

[11] Patent Number: 5,618,295
[45] Date of Patent: Apr. 8, 1997

[54] APPARATUS FOR PREPARING SKIN IN ADVANCE

[75] Inventor: Jin K. Min, Kyungki-do, Rep. of Korea

[73] Assignee: Samsung Electro-Mechanics Co., Ltd., Kyungki-do, Rep. of Korea

[21] Appl. No.: 322,494

[22] Filed: Oct. 14, 1994

[30] Foreign Application Priority Data

Oct. 16, 1993 [KR] Rep. of Korea ............... 93-21511
Oct. 16, 1993 [KR] Rep. of Korea ............... 93-21512
Oct. 16, 1993 [KR] Rep. of Korea ............... 93-21513

[51] Int. Cl.⁶ ............................................. A61B 17/00
[52] U.S. Cl. ............................. 606/171; 606/186; 606/1
[58] Field of Search ............................. 606/167, 171, 606/185, 186, 1; 604/46, 173, 156, 151; 128/743, 744, 754

[56] References Cited

U.S. PATENT DOCUMENTS 2,009,562  7/1935  Okumura ..................... 606/186 X
3,086,530  4/1963  Groom ......................... 606/186 X
4,437,361  3/1984  Steckel et al. ............... 606/186 X
5,415,182  5/1995  Chin et al. .................... 128/754

FOREIGN PATENT DOCUMENTS 2903159   7/1980   Germany ..................... 606/186
76053    10/1954   Netherlands ................ 606/186
92-2264   3/1992   Rep. of Korea .
396311    1/1966   Switzerland ................. 604/46
720794   12/1954   United Kingdom ........... 604/46

Primary Examiner—Guy V. Tucker
Attorney, Agent, or Firm—Lowe, Price, LeBlanc & Becker

[57] ABSTRACT

An apparatus for preparing skin in advance to administer insulin to a body of a diabetic by forming a plurality of cicatrices on the skin is disclosed. The apparatus includes a rotatable skin needle assembly having a plurality of skin needles thereon. The assembly is vertically vibrated by the interaction of a coil and magnet and is rotated by a motor and/or reduction gears.

10 Claims, 9 Drawing Sheets

APPARATUS FOR PREPARING SKIN IN ADVANCE

FIELD OF THE INVENTION

This invention relates to a medical instrument and more particularly to an apparatus for preparing skin in advance by forming a plurality of cicatrices thereon to administer insulin to a body of a patient, for example, a diabetic et al.

BACKGROUND OF THE INVENTION

Generally, insulin is used to treat patients, in particular, diabetics for their recovery. The insulin is composed of high polymers with a molecular weight of 6000 or more and has a strong hydrophilic property with peptide bonds of amino acids. Therefore, the insulin is difficult to administer to a body through the epidermis of the skin even if the skin is transformed in properties by chemical solvents.

Also, the hydrophilic insulin is not chemically compatible with the epidermis having a hydrophobic property. For the above reasons, it is known that it is difficult for the insulin to permeate into the skin.

The skin of the body consists of three layers, namely, epidermis, scleroid layer, and derma. The epidermis as outer skin has the least permeation of medical substances and is composed of 2% lipid and 40% protein, and has 0.1 mm or more thickness. The epidermis has a hydrophobic property because each segment of the protein of the epidermis is enclosed with the lipid. Further, in comparison with water contents, those of the derma and the scleroid layer are 70% or more, respectively, and that of epidermis is about 40%. As a result, the epidermis has high electric resistance and protects the derma from heat stimulation and any other external stimulation.

On the other hand, known methods for administering the insulin to the body of the diabetic through the skin are classified into three large types, ointment-type, patch-type, and spray-type. Among the types; the patch-type methods have been actively researched and developed in recent years.

As a prior art, an instrument of the patch-type for administering insulin to the scleroid layer of the skin is disclosed in Korean Patent Publication No. 92-2264, which is incorporated herein by reference. Referring to FIG. 1, showing the above instrument, the instrument comprises a case 1 which stores insulin and solvent therein, a high polymer support 2 which has a water swelling property and on which the insulin is distributed in a powdered state, a skin needle support 3 showing a swelling property in accordance to the discharge of the solvent after the adhesion of the instrument to the skin, a plurality of skin needles 4 which are arranged fixedly and vertically on the support 3 to contact the skin, and an electrode 5 which is provided within the case 5 to apply an electric current.

According to the above configuration, firstly, the instrument is adhered to the skin to bring the needles 4 of the skin needle support 3 into contact with the skin. The, the passages formed by the needles 4 are temporarily closed by the swell of the skin. When the direct current or ripple current is applied to the electrode 5, the ionized insulin and the solvent are moved toward the opposite electrode. At this time, the hydrophilic protein and polypeptide of the skin are parallel and contractedly arranged toward the positive electrode. Thereafter, the passages of the epidermis are opened to permeate the insulin to the derma.

On the other hand, explaining the reason that a plurality of skin needles are used in the prior art instrument, it is that the skin needles penetrate only the epidermis of the skin to permit easy flow of the insulin from the epidermis via the scleroid layer and the derma into the capillary vessels. Therefore, the amount of insulin administered to the body is increased.

However, in the prior art instrument as mentioned above, a plurality of skin needles, are fixedly arranged on the skin needle support which shows the swelling property in accordance to the discharge of the insulin and solvent. Accordingly, it is difficult to make the skin needles of 50 to 400 μm in diameter. Also, the support being formed of materials with swelling property makes the manufacturing cost of the prior art instrument higher.

Further, there exists a problem that the prior art instrument is used only one time because the instrument is not a re-usable single set which comprises a case and a support. Furthermore, generally, thousands of skin needles are required to quickly administer the insulin to the body of the patient. However, hundreds of skin needles may be fixed to the support according to the prior art instrument. Therefore, there are disadvantages that the patient, who adheres the insulin patch to his skin for a long time, feels a pain and must be prudent in his conduct.

SUMMARY OF THE INVENTION

It is an object of the present invention to provide an apparatus for preparing skin in advance to administer insulin to a body of a diabetic by forming a plurality of cicatrices on the skin and thereafter adhering a separate insulin patch to the skin.

To achieve the above-mentioned object, there is provided an apparatus comprising a housing; a rotatable skin needle assembly having a plurality of skin needles thereon, the assembly being provided at one end of the housing and being moved upward and downward; a power supply; a device for moving the assembly upward and downward in accordance with operation of the power supply; and a device for rotating the assembly by predetermined rotations in accordance with operation of the power supply.

In a first embodiment of the present invention, the device for moving the assembly upward and downward comprises an inner yoke and an out yoke; a magnet provided between the yokes to generate magnetic force through a gap forming magnetic paths between the yokes; a coil guide winding a coil therearound; a shaft rod guide for guiding the shaft rod; wherein the device for moving the assembly upward and downward is operated by means of interaction of the coil and the magnet. Preferably, an electric member is fitted between the coil guide and the shaft rod guide to elastically move the assembly.

In a second embodiment of the present invention, first coil spring is provided between the inner yoke and the coil guide, and second coil spring is provided between the coil guide and the shaft rod guide to elastically move the assembly.

Further, the devices for rotating the assembly according to the present invention may be made in various configuration. First, the device comprises a low speed motor, and a coupling for coupling a shaft of the motor to a yoke shaft to which an outer yoke is rotatably mounted. Second, the device comprises a low speed motor; a rotatable outer yoke having an internal gear thereon; and a pinion mounted to a shaft of the motor and engaged with the internal gear to rotate the outer yoke. Third, the device comprises a motor;

planetary gears connected to a shaft of the motor to reduce rotating force of the motor; a rotatable outer yoke connected to the planetary gears; and a yoke guide enclosing the outer yoke and rotating the assembly. In this embodiment, the planetary gears comprises a sun gear mounted to the shaft of the motor, a plurality of planet gears to reduce rotating force of the sun gear, and an internal gear engaged with the planet gears.

Further, preferably, ring-type contact members may be provided at periphery of the yoke guide to supply a coil with electric current, and elastic contact members may be provided at inside peripheral surface of the housing to contact the ring-type contact members.

BRIEF DESCRIPTION OF THE DRAWINGS

These and other features and advantages of the present invention will be better understood by reference to the following detailed description when considered in conjunction with the accompanying drawings therein.

DETAILED DESCRIPTION OF THE PREFERRED EMBODIMENT

Figure 2:
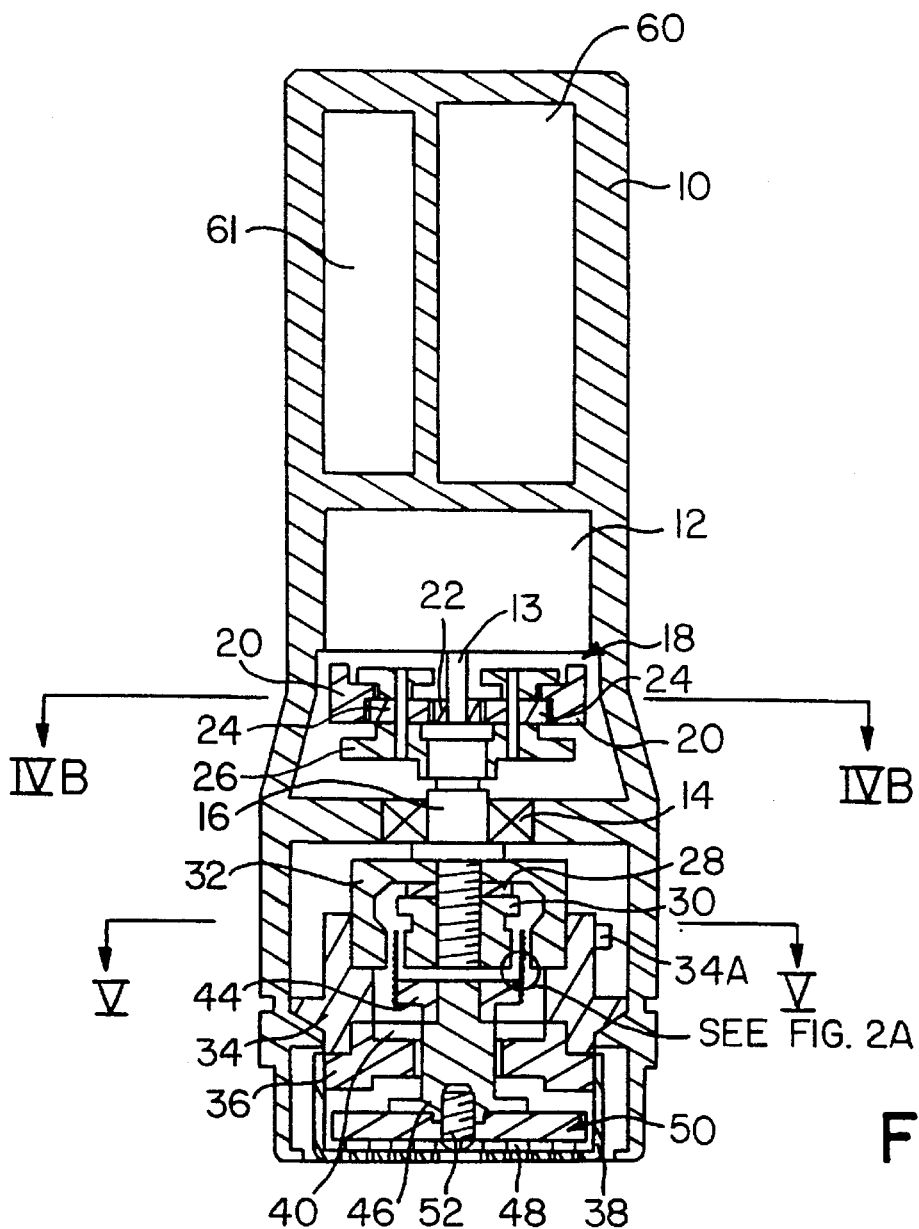
FIG. 2 is a side sectional view of an apparatus constructed in accordance with a first embodiment of the present invention.
Figure 2A:
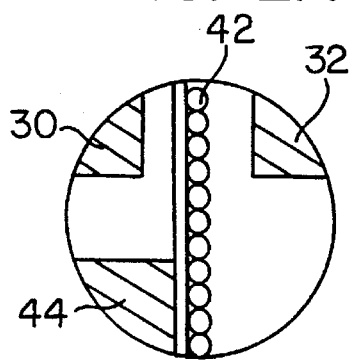
FIG. 2A is an enlarged view of a portion of the side sectional view of FIG. 2.
Figure 4A:
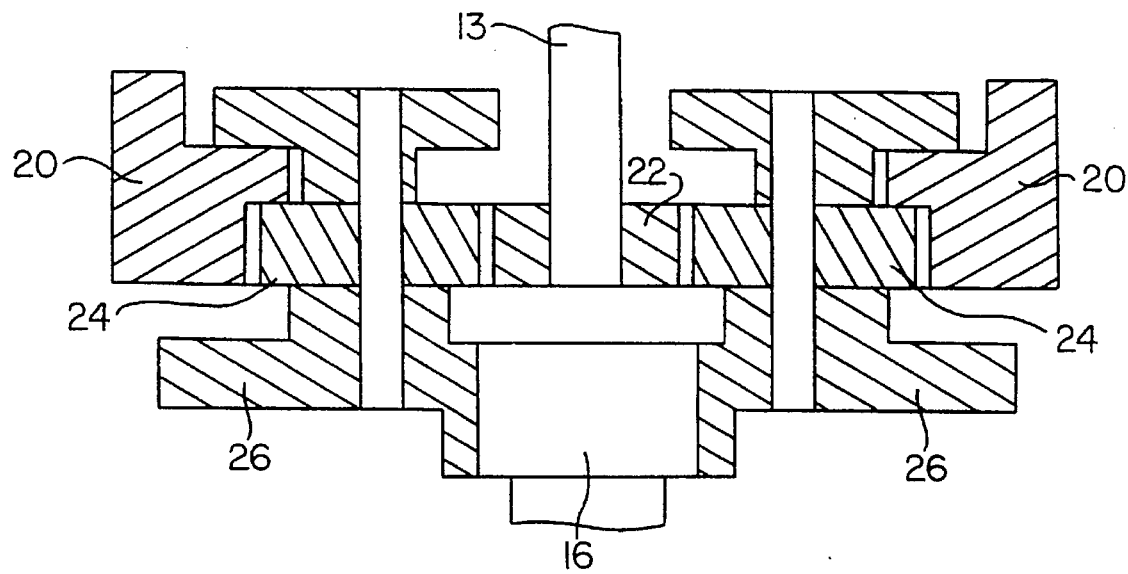
FIG. 4A is an enlarged side view illustrating planetary gears of FIG. 2.
Figure 4B:
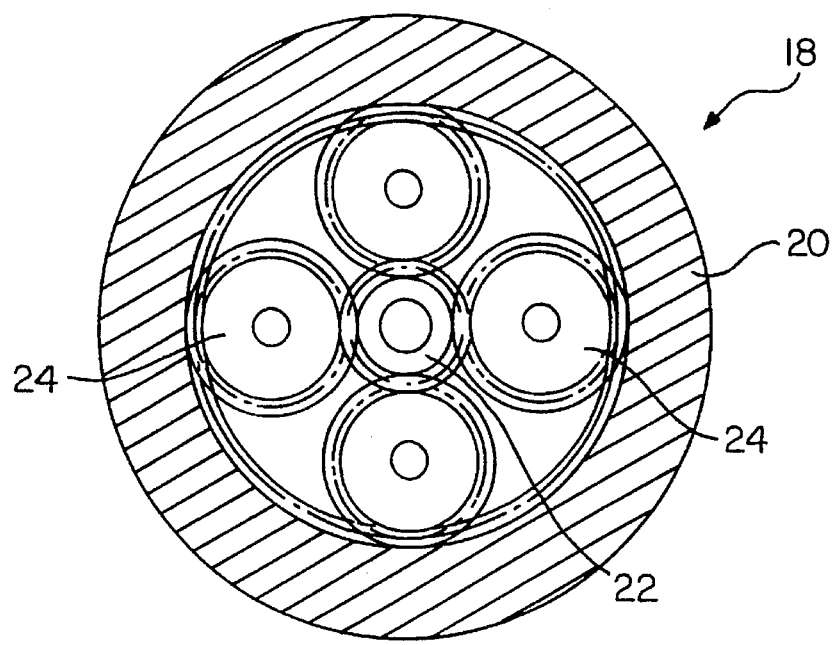
FIG. 4B is a sectional view of the apparatus shown in FIG. 2, taken through line IV B—IV B.

Referring to FIG. 2, in a first embodiment of the present invention, a motor 12 is mounted within a housing 10. A shaft 13 of the motor 12 is coupled to a yoke shaft 16 which is rotatably supported by a bearing 14. Referring to FIG. 4B, planetary gears 18 comprises a sun gear 22, four planet gears 24 to reduce rotating force of the sun gear 22, and an internal gear 20 engaged with the planet gears 24 which are rotatably mounted on a gear mounting plate 26. As depicted in FIG. 4A, the shaft 13 of the motor 12 is fixedly connected to the sun gear 22, and the yoke shaft 16 is connected to the gear mounting plate 26. Referring again to FIG. 2, an inner yoke 30 and an outer yoke 32 is mounted to the yoke shaft 16. A magnet 28 is provided between the yokes 30 and 32 to generate magnetic force. A yoke guide 34 and a shaft rod yoke 32, and a needle plate guide 38 are provided at the outside of the shaft rod guide 36.

Figure 6:
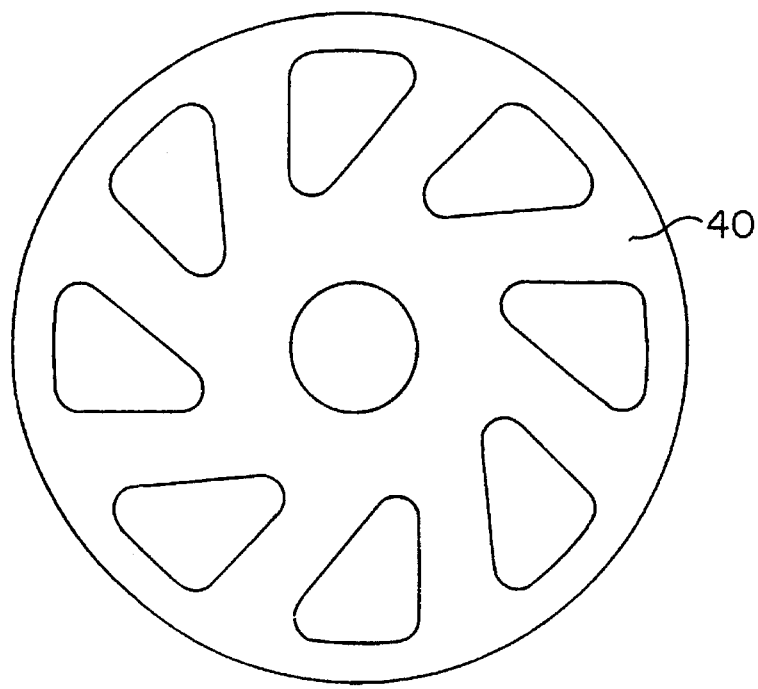
FIG. 6 is a plan view of a plate spring of FIG. 2.

As best depicted in FIG. 4A, a coil guide 44 is provided with the yoke guide 34. A coil 42 is wound around a gap which is formed between the internal yoke 30 and the outer yoke 32. Also, a part of the coil 42 is wound around an upper end of the coil guide 44. A shaft rod 46 is slidably fitted with the coil guide 44. A plate spring 40 as shown in FIG. 6 is fitted between the coil guide 44 and the shaft rod guide 36.

Figure 1:
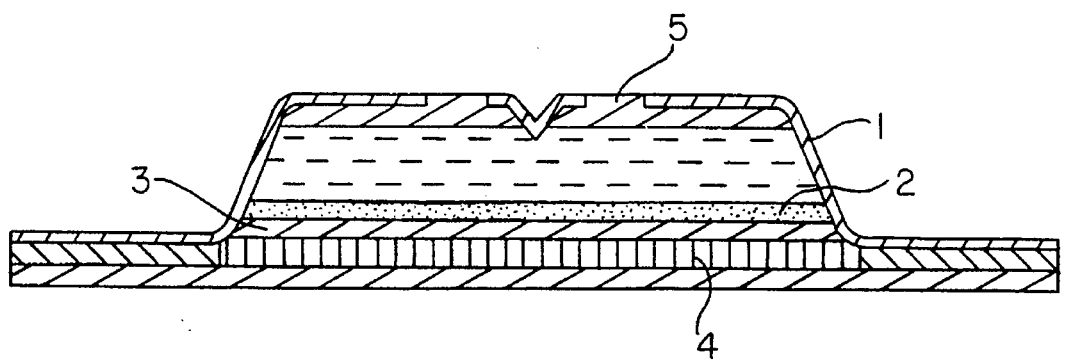
FIG. 1 is a side sectional view of a prior art instrument for administering insulin to the scleroid layer of skin.
Figure 3A:
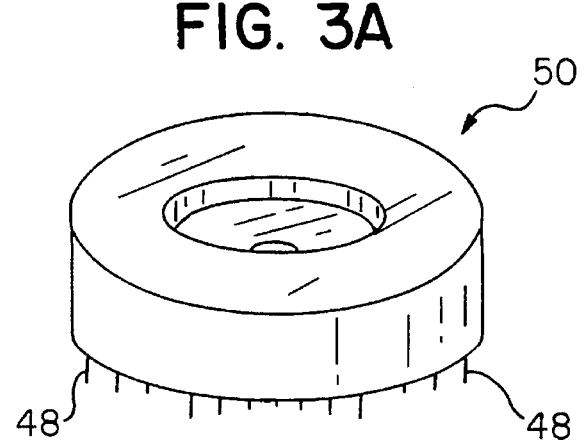
FIG. 3A is a perspective view illustrating schematically a skin needle assembly of FIG. 2.

As shown in FIG. 3, a skin needle assembly 50 is fixed to the shaft rod guide 36 via a screw 52 and is provided with hundreds of skin needles thereon. Further, referring to FIG. 5, a contact protrusion 34A is formed at the outer surface of the yoke guide 34 and a plurality of limit switches 34B is formed at the inner surface of the housing 10 to switch the rotating direction of the motor 12 within the range of a predetermined angle. On the other hand, a battery (not shown) and a controller (not shown) are mounted within the housing 10 in predetermined positions to drive the motor 12 and to supply the coil 42 with power supply.

Now, the operation of the first embodiment according to the present invention with the above configuration will be explained in detail.

First, the needle plate guide 38 of the apparatus is contacted to a predetermined position of the skin. A switch (not shown) which is provided at the outside of the housing 10 is operated in the state that the direct-current magnetic flux of the magnet 28 maintains in a flux linkage. Then, the coil 42, provided above the yoke guide 34, generates an indirect-current magnetic flux to be moved upward and downward according to Fleming's rule.

According to the vertical vibration of the coil 42, the coil guide 44 and the shaft rod 46 which are formed integral with the coil 42 are elastically and vertically vibrated by the plate spring 40. The frequency number of the coil guide 44 and the shaft rod 46 is more than that of the skin, for example, about 20 Hz. Therefore, the skin needle assembly 50 is also vertically vibrated by the vibration of the shaft rod 46. As a result, the assembly 50 penetrates only the epidermis of the skin to form a plurality of cicatrices on the skin. At this time, the current applied to the coil 42 is settled by the controller so that the skin needle assembly 50 is vertically vibrated three times.

Simultaneously, the motor 12 mounted with the housing 10 is driven to transmit the driving force to the yoke shaft 16 and to rotate the plurality of skin needles 48 of the skin needle assembly 50. The rotations of the shaft 13 of the motor 12 are reduced by the planetary gears 18. Accordingly, because the skin needle assembly 50 is vertically vibrated and simultaneously is rotated, a plurality of cicatrices is uniformly and effectively formed on the skin.

On the other hand, according to the arrangement of the skin needles 48, the skin needle assembly 50 is rotated between the plurality of limit switches 34B within the range of one revolution. Large torque is required to bear the contact resistance with the skin.

Summing up, under the control of the controller, the current is applied to the coil 42 to vertically vibrate the skin needle. assembly 50 three times. Thereafter, the controller shuts off the current being applied to the coil 42 and supplies the motor 12 with the current. The motor 12, preferably as a stepping motor, is rotated within the range of a predetermined angle and then is stopped. The rotating angle of the motor 12 is designed to form a plurality of cicatrices on the skin.

Figure 3B:
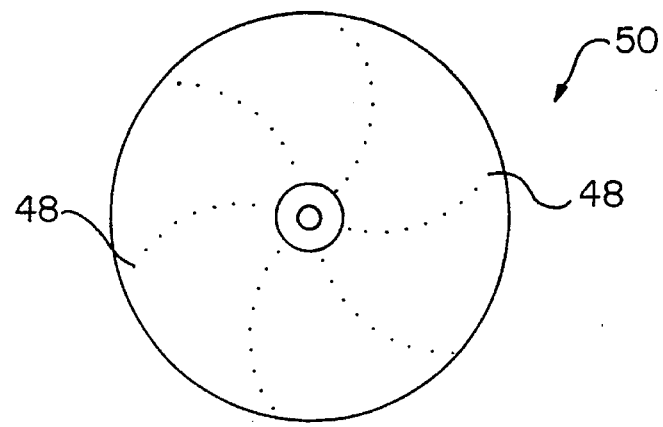
FIG. 3B is a view illustrating an arrangement of a plurality of skin needles of the skin needle assembly of FIG. 3A.

As shown in FIG. 3B, the number of the skin needles 48 formed on the assembly 50 is limited to tens or hundreds. Thus, by driving the motor 12 to rotate the skin needle assembly 50, the desired result of forming thousands of cicatrices on the skin is obtained. Thereafter, the insulin patch is adhered to the formed skin. Accordingly, the insulin is easily and quickly administered to the capillary vessels of the body from thousands of cicatrices via the epidermis, the scleroid layer and the derma.

Figure 7:
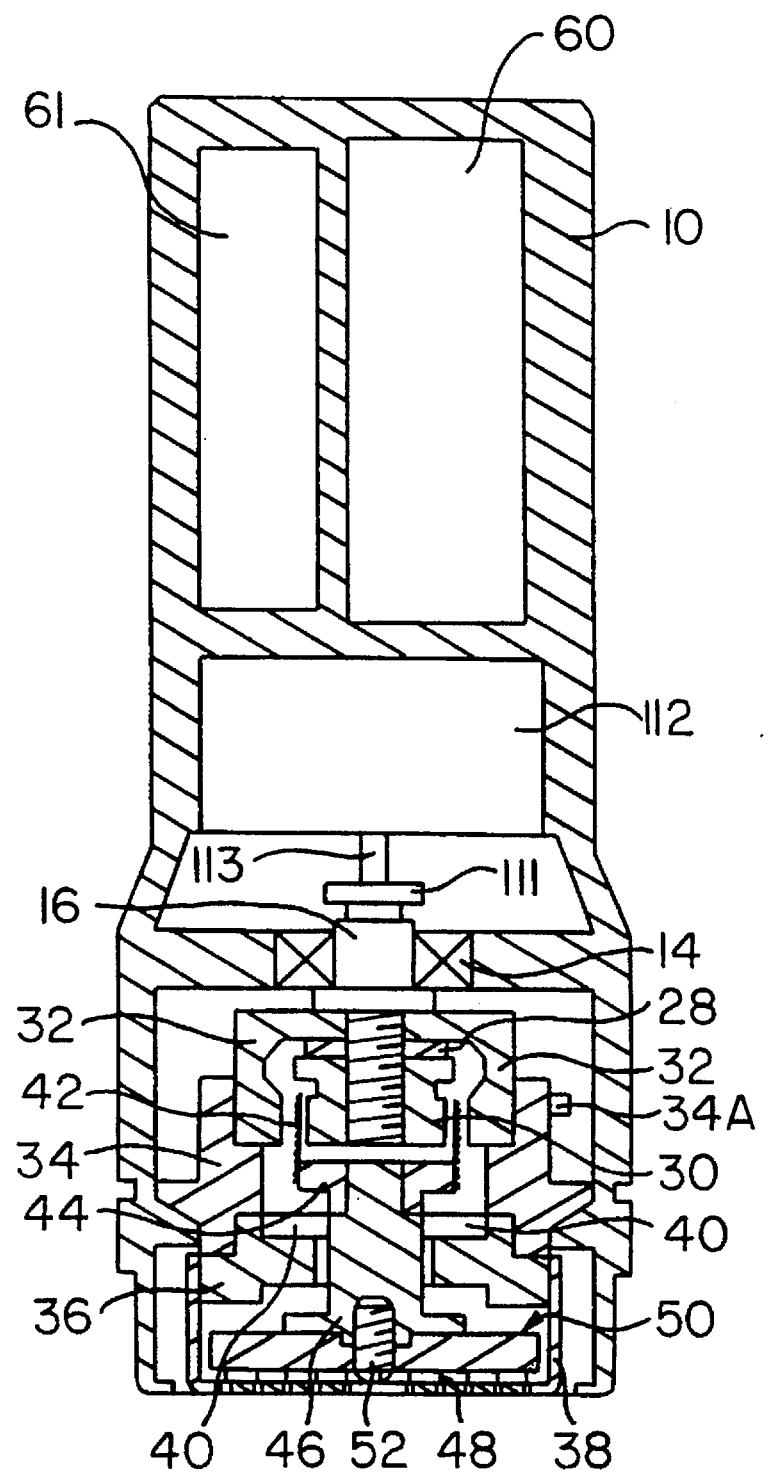
FIG. 7 is a side sectional view of an apparatus constructed in accordance with a second embodiment of the present invention.

Now referring to FIG. 7, in a second embodiment of the present invention, it is desirable to use a low speed motor as a motor 112. A shaft 113 of the motor 112 is directly connected to the yoke shaft by means of a coupling 114. Therefore, according to the second embodiment, thousands of cicatrices are formed on the skin by means of the vertical vibration of the skin needles 48 and the low rotation of the motor 112. The vertical vibration of the skin needles 48 is accomplished by the interaction of the coil 42 and the magnet 28 as mentioned in the first embodiment.

Figure 8:
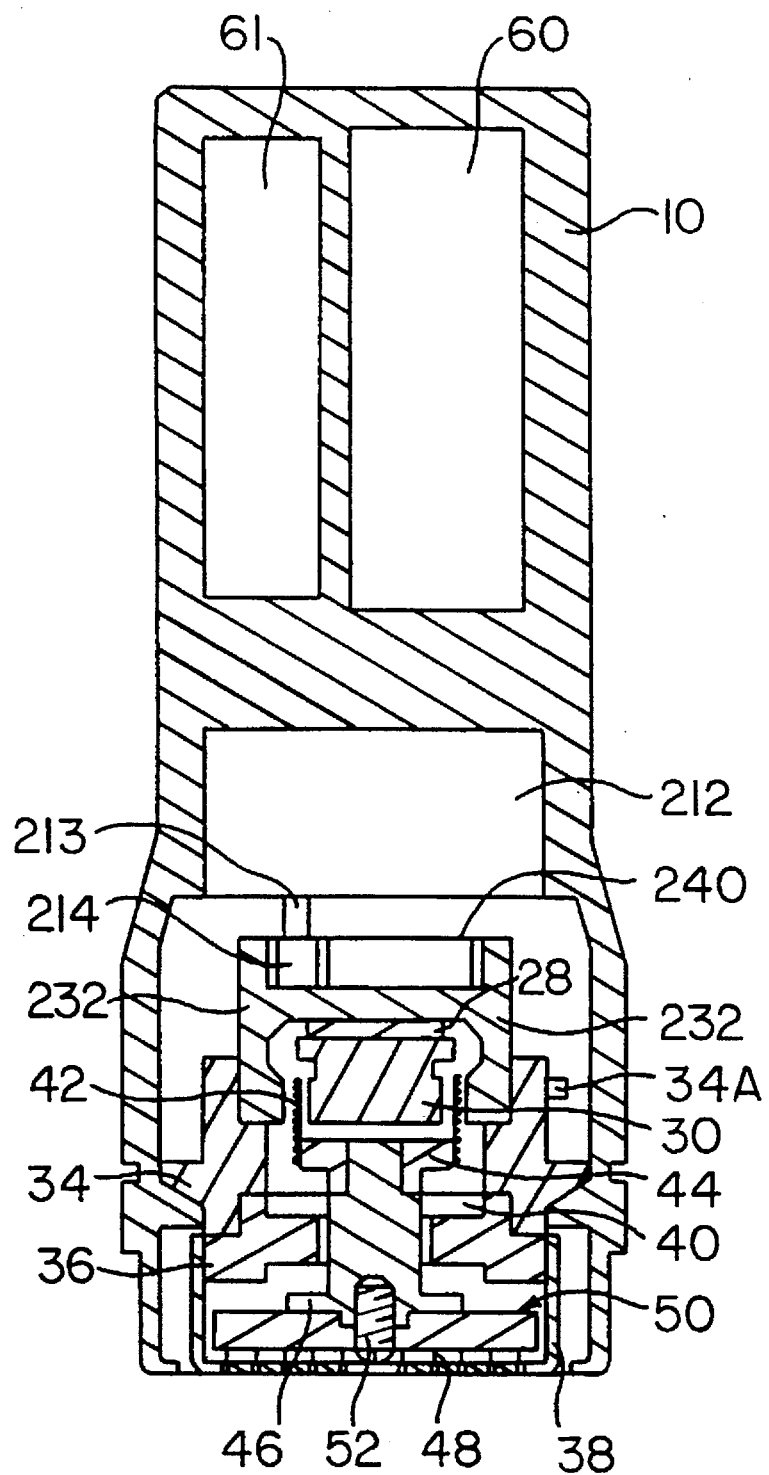
FIG. 8 is a side sectional view of an apparatus constructed in accordance with a third embodiment of the present invention.

Referring to FIG. 8, in a third embodiment of the present invention, a shaft 213 of a motor 212 is eccentrically mounted about the center of the housing 10. A pinion 214 is mounted to the shaft 213. An outer yoke 232 is provided with an internal gear 240 thereon to be engaged with the pinion 214.

Figure 5:
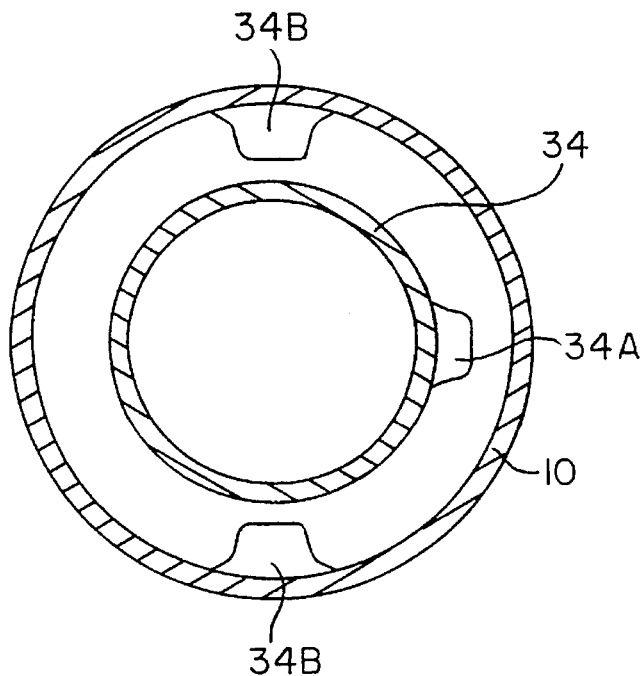
FIG. 5 is a sectional view of the apparatus shown in FIG. 2, taken through line V—V.
Figure 9:
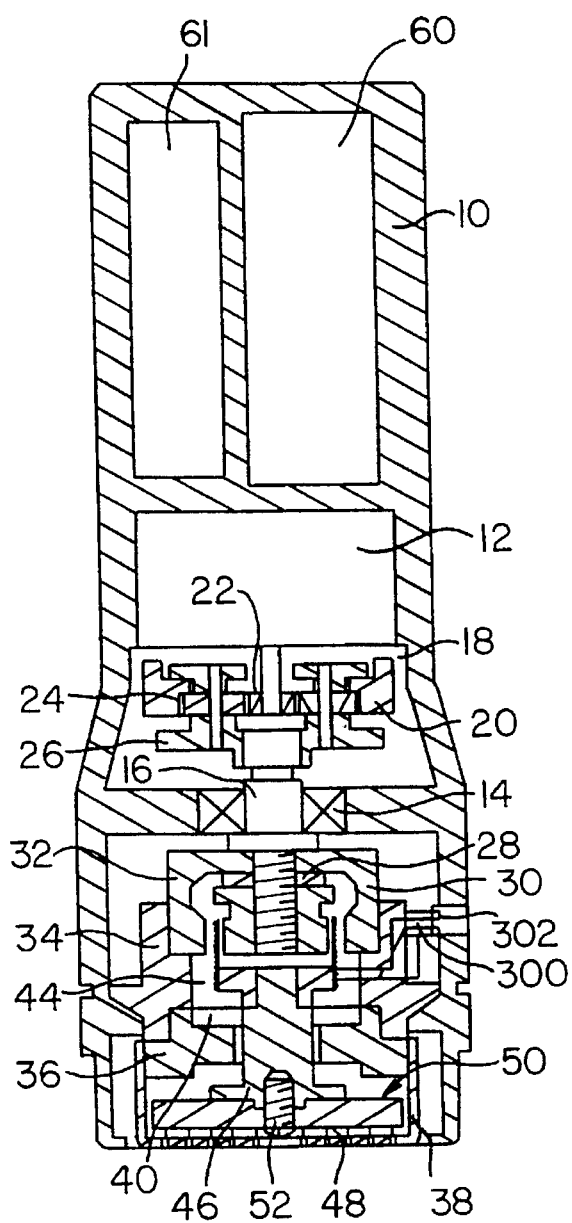
FIG. 9 is a side sectional view of an apparatus constructed in accordance with a fourth embodiment of the present invention.
Figure 10:
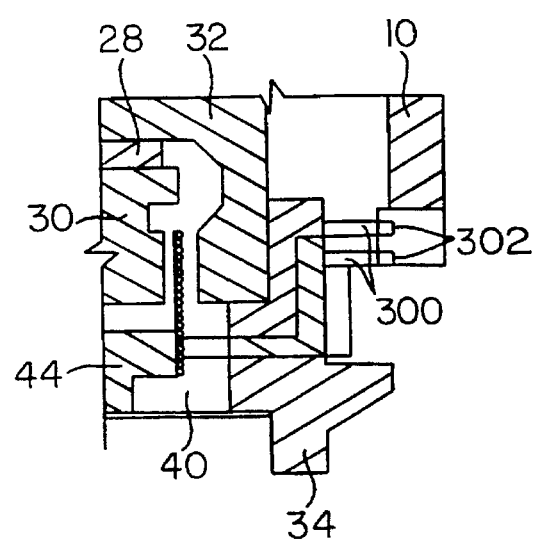
FIG. 10 is an enlarged sectional view of main parts of the apparatus shown in FIG. 9.

Referring to FIG. 9 and FIG. 10, in a fourth embodiment of the present invention, the fourth embodiment are to improve the disadvantages of the first embodiment. As shown in FIG. 5, the contact protrusion 34A of the yoke guide 34 is reciprocatedly rotated between the limit switches of the housing 10. Thus, the current may be applied to the coil 42 which is vertically vibrated and is rotated, however, the skin needles 48 of the skin needle assembly 50 may be limited in their arrangement.

Figure 11:
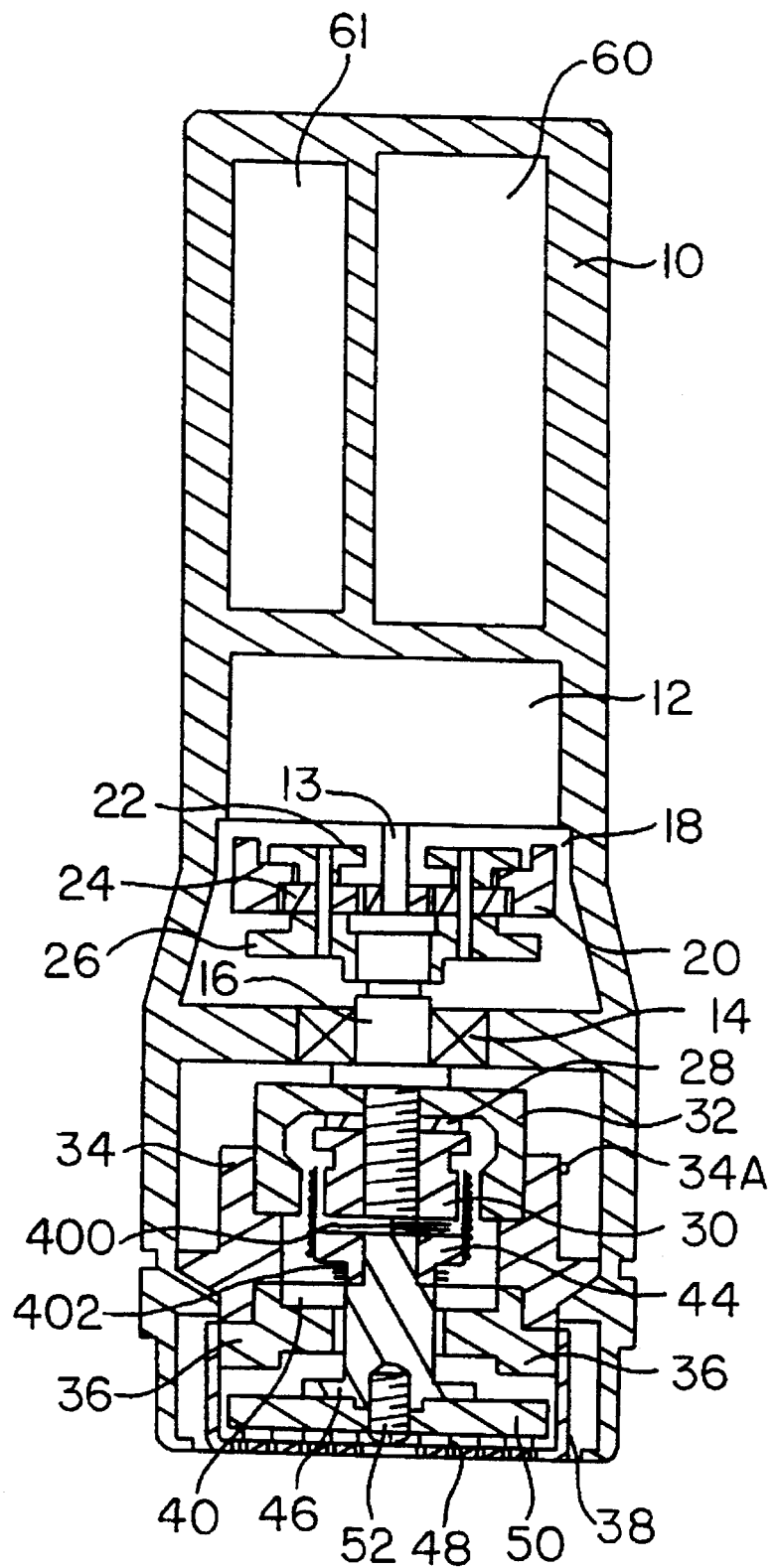
FIG. 11 is a side sectional view of an apparatus constructed in accordance with a fifth embodiment of the present invention.
Figure 12:
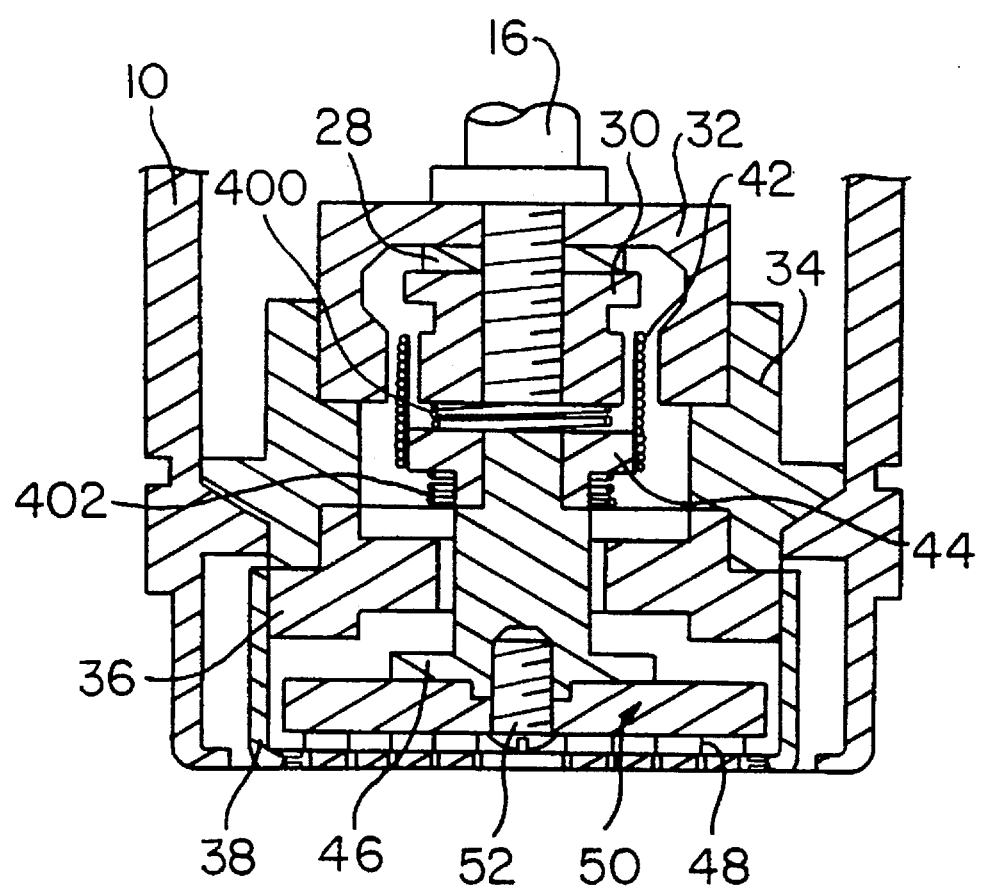
FIG. 12 is an enlarged sectional view of main parts of the apparatus shown in FIG. 11.

As shown in FIG. 9 and FIG. 10, ring-type contact members 300 are provided at periphery of the yoke guide 34 and are connected to the ends of the coil 42. Elastic contact members 302 are provided at inside peripheral surface of the housing 10 to contact the ring-type contact member 300. Therefore, the current may be applied to the coil 42 while the coil guider 44 is rotated continuously in one direction. As a result, the disconnection of the coil 42 and the overload of the motor 12 may be prevented, and in particular the skin needles 48 may be freely arranged on the skin needle assembly 50. Referring to FIG. 11 and FIG. 12, in a fifth embodiment of the present invention, the fifth embodiment is also to improve the disadvantages of the first embodiment in the same manner as the fourth embodiment.

In the first embodiment of the present invention, the plate spring 40 has an shape as shown in FIG. 6 and is provided between the shaft rod guide 36 and the coil guide 44. Also, the plate spring 40 is fitted with the shaft rod 46. Thus, the shaft rod guide 36 and the coil guide 44 have a plurality of stepped parts to be fitted with the plate spring 40. Further, the coil guide 44 and the shaft rod 46 may not be vertically vibrated within the desirable range of the natural frequency of the skin because the shaft rod 46 is fitted with the coil guide 44 via the plate spring 40.

In the fifth embodiment of FIG. 11 and FIG. 12, first coil spring 400 is provided between the inner yoke 30 and the coil guide 44, and second coil spring 402 is provided between the coil guide 44 and the shaft rod guide 36 to elastically move the skin needle assembly 50. Accordingly, the assembly 50 fixed to the shaft rod 46 can be vertically vibrated with ease at the frequency adjacent to the natural frequency of the skin. Large output can be obtained by small input.

What is claimed is:

1. An apparatus for preparing skin in advance by forming a plurality of cicatrices thereon to administer insulin to a patient, said apparatus comprising:

a housing;

a rotatable skin needle assembly having a plurality of skin needles thereon, said assembly being located at one end of said housing and being moved upward and downward;

a power supply;

means powered by said power supply for vibrating said assembly upwardly and downwardly relative to said housing; and means powered by said power supply for rotating said assembly by predetermined rotations.

2. An apparatus as claimed in claim 1, wherein said means for vibrating said assembly comprises:

an inner yoke and an outer yoke;

a magnet provided between said yokes to generate magnetic force through a gap forming magnetic paths between said yokes;

a coil guide winding a coil therearound;

a shaft rod connected to said coil guide and said assembly, respectively; and a shaft rod guide for guiding said shaft rod;

wherein said means for vibrating said assembly is operated by means of interaction of said coil and said magnet.

3. An apparatus as claimed in claim 2, wherein an elastic means is fitted between said coil guide and said shaft rod guide to elastically move said assembly.

4. An apparatus as claimed in claim 2, wherein first coil spring is provided between said inner yoke and said coil guide, and second coil spring is provided between said coil guide and said shaft rod guide to elastically move said assembly.

5. An apparatus as claimed in claim 1, wherein said means for rotating said assembly comprises a low speed motor, and means for coupling a shaft of said motor to a yoke shaft to which an outer yoke is rotatably mounted.

6. An apparatus as claimed in claim 5, wherein said means for rotating said assembly further comprises a bearing to exactly transmit rotating force of said motor to the outer yoke.

7. An apparatus as claimed in claim 1, wherein said means for rotating said assembly comprises:

a low speed motor;

a rotatable outer yoke having an internal gear thereon; and a pinion mounted to a shaft of said motor and engaged with the internal gear to rotate said outer yoke.

8. An apparatus for preparing skin in advance by forming a plurality of cicatrices thereon to administer insulin to a patient, said apparatus comprising:

a housing;

a rotatable skin needle assembly having a plurality of skin needles thereon, said assembly being located at one end of said housing and being moved upward and downward;

a power supply;

means powered by said power supply for vibrating said assembly upwardly and downwardly relative to said housing; and means powered by said power supply for rotating said assembly by predetermined rotations wherein said means for rotating said assembly comprises:

a motor;

planetary gears connected to a shaft of said motor to reduce rotating force of said motor;

a rotatable outer yoke connected to said planetary gears; and a yoke guide enclosing said outer yoke and rotating said assembly.

9. An apparatus as claimed in claim 8, wherein planetary gears comprises a sun gear mounted to the shaft of said motor, a plurality of planet gears to reduce rotating force of the sun gear, and an internal gear engaged with the planet gears.

10. An apparatus as claimed in claim 8, wherein ring-type contact members are provided at periphery of said yoke guide to supply a coil with electric current, and elastic contact members are provided at inside peripheral surface of said housing to contact the ring-type contact members.

* * * * *